(12) United States Patent
Takahashi

(10) Patent No.: US 10,351,451 B2
(45) Date of Patent: Jul. 16, 2019

(54) OZONE WATER AND METHOD FOR PRODUCING THE SAME

(71) Applicant: National Institute of Advanced Industrial Science and Technology, Tokyo (JP)

(72) Inventor: Masayoshi Takahashi, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/500,290

(22) PCT Filed: Aug. 1, 2015

(86) PCT No.: PCT/JP2015/071896
§ 371 (c)(1),
(2) Date: Jan. 30, 2017

(87) PCT Pub. No.: WO2016/017821
PCT Pub. Date: Feb. 4, 2016

(65) Prior Publication Data
US 2017/0210650 A1    Jul. 27, 2017

(30) Foreign Application Priority Data
Aug. 1, 2014 (JP) ................ 2014-158263

(51) Int. Cl.
| | | |
|---|---|---|
| A61L 9/01 | (2006.01) | |
| C02F 1/78 | (2006.01) | |
| C01B 13/10 | (2006.01) | |
| B01F 3/04 | (2006.01) | |
| B01F 5/00 | (2006.01) | |
| C02F 1/50 | (2006.01) | |
| C02F 1/68 | (2006.01) | |

(52) U.S. Cl.
CPC ........ *C02F 1/78* (2013.01); *A61L 9/01* (2013.01); *B01F 3/04113* (2013.01); *B01F 5/0057* (2013.01); *C01B 13/10* (2013.01); *C02F 1/50* (2013.01); *C02F 1/68* (2013.01); *B01F 2003/04858* (2013.01); *B01F 2003/04886* (2013.01); *B01F 2215/008* (2013.01); *C02F 2201/784* (2013.01); *C02F 2303/02* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 8,137,703 B2 * | 3/2012 | Chiba | ............. A61L 2/183 210/150 |
| 2006/0016763 A1 | 1/2006 | Kerfoot | |
| 2007/0205161 A1 | 9/2007 | Chiba | |
| 2011/0300239 A1 * | 12/2011 | Hasegawa | ........... A61K 9/0095 424/719 |

FOREIGN PATENT DOCUMENTS

| | | |
|---|---|---|
| CN | 101514043 A | 8/2009 |
| JP | 2005-245817 A1 | 9/2005 |
| JP | 2005-246293 A1 | 9/2005 |
| JP | 2007-275089 A1 | 10/2007 |
| WO | 01/45869 A2 | 6/2001 |
| WO | 2006/020262 A2 | 2/2006 |
| WO | 2008/072371 A1 | 6/2008 |
| WO | 2010004653 A1 | 1/2010 |

OTHER PUBLICATIONS

Extended European Search Report for counterpart EPC Patent Application No. 15827201.3, dated Feb. 21, 2018 (10 Sheets).
International Search Report for International Application No. PCT/JP2015/071896 dated Oct. 20, 2015.
Office Action of New Zealand Patent Application No. 728866: First Examination Report dated Jun. 21, 2018 (6 pages).
N. Kishimoto, et al.; "Catalytic Effect of Several Iron Species on Ozonation"; Journal of Water and Environment Technology; vol. 10; No. 2; 2012; pp. 205-215 (11 pages).
E. Rodriguez, et al.; "TiO2 and Fe (III) photocatalytic ozonation processes of a mixture of emergent contaminants of water"; Water Research; vol. 46(1); 2012; pp. 152-166 (15 pages).
J. Lee, et al.; "Catalytic Ozonation of Humic Acids with Fe/MgO"; Korean Journal of Chemical Engineering; vol. 22(4); 2005; pp. 536-540 (5 pages).
A. Ahmed, et al.; "Decomposition of Carboxylic Acids in Water by O3, O3/H2O2, and O3/Catalyst"; Ozone: Science and Engineering; vol. 27(1); 2005; pp. 11-18 (8 pages).
E. Portjanskaja; "Ozone Reactions with Inorganic and Organic Compounds in Water"; Ozone Science and Technology; © Encyclopedia of Life Support Systems (EOLSS).

* cited by examiner

*Primary Examiner* — David J Blanchard
*Assistant Examiner* — Daniel F. Coughlin
(74) *Attorney, Agent, or Firm* — Kratz, Quintos & Hanson, LLP

(57) ABSTRACT

An object of the present invention is to provide an ozone water having enhanced storage stability and a method for producing the ozone water. An ozone water of the present invention as a means for resolution is produced by dissolving 0.1 µM to 1 mM of an organic iron compound and 1 to 300 mM of an inorganic salt in a water with ozone-microbubbles generated using an ozone gas at a concentration of 1 to 300 g/Nm$^3$. The half-life of ozone of the ozone water of the present invention is 3 days or longer, for example, when the water filled in an airtight container under atmospheric pressure is stored under a temperature condition of 40° C.

8 Claims, No Drawings

OZONE WATER AND METHOD FOR PRODUCING THE SAME

TECHNICAL FIELD

The present invention relates to an ozone water and a method for producing the ozone water.

BACKGROUND ART

Although ozone, which has an oxidative effect, a sterilizing effect, a deodorant effect, and the like, is expected for use in various fields, due to the form of gas, ozone lacks versatility when directly used. Accordingly, in order to effectively utilize ozone, for example, ozone has to be dissolved in water to be used as an ozone water. However, ozone has drawbacks of essentially low solubility in water and a very short half-life in the state of being dissolved in water. For this reason, ozone is currently used after ozone gas is dissolved in water at the site of use by a method such as bubbling. Such a method, however, has a problem of a production apparatus of ozone water required to be brought to the site of ozone use, and problems of the cost and countermeasures against exhaust ozone. Accordingly, the practical use of ozone has not become common yet.

Thus, the present inventor proposes, in Patent Document 1, as a method for drastically improving low storability of ozone water which is a drawback thereof, a technique for securing long-term storability while maintaining the effects of ozone, by utilizing ozone bubbles of nano-sizes (ozone nanobubbles). However, further enhancement is demanded in storage stability of ozone water at the site of ozone use.

PRIOR ART DOCUMENTS

Patent Document

Patent Document 1: JP-A-2005-246293

SUMMARY OF THE INVENTION

Problems that the Invention is to Solve

Thus, an object of the present invention is to provide an ozone water having enhanced storage stability and a method for producing the ozone water.

Means for Solving the Problems

As a result of intensive studies in view of the above problems, the present inventor has found that when prescribed amounts of an organic iron compound and an inorganic salt are dissolved in a water with ozone-microbubbles generated using an ozone gas at a prescribed concentration, it is possible to enhance storage stability of the ozone water.

An ozone water of the present invention made on the basis of the above findings is, as described in a first embodiment, produced by dissolving 0.1 µM to 1 mM of an organic iron compound and 1 to 300 mM of an inorganic salt in a water with ozone-microbubbles generated using an ozone gas at a concentration of 1 to 300 g/Nm³.

An ozone water described in a second embodiment is the ozone water according to the first embodiment, in which the organic iron compound is at least one selected from the group consisting of iron ammonium citrate, iron fulvate, iron acetate, heme iron, iron dextran, diethylenetriaminepentaacetic acid iron sodium salt, diethylenetriaminepentaacetic acid iron ammonium salt, ethylenediaminetetraacetic acid iron sodium salt, ethylenediaminetetraacetic acid iron ammonium salt, iron triethylenetetramine, dicarboxymethylglutamic acid iron sodium salt, ferrous citrate, iron sodium citrate, iron oxalate, ferrous succinate, iron sodium succinate citrate, ferrous pyrophosphate, ferric pyrophosphate, iron lactate, ferrous gluconate, ferrous formate, ferric formate, potassium ferric ammonium oxalate, ferrous ascorbate, and sodium ferric edetate.

An ozone water described in a third embodiment is the ozone water according to the first embodiment, in which the inorganic salt is at least one or more selected from the group consisting of sodium chloride, potassium chloride, magnesium chloride, and magnesium sulfate.

An ozone water described in a fourth embodiment is the ozone water according to the first embodiment, in which the generation of ozone-microbubbles is achieved by using a microbubble generator that can generate microbubbles having a particle size of 5 to 50 µm.

An ozone water described in a fifth embodiment is the ozone water according to the fourth embodiment, in which the microbubble generator is a microbubble generator that employs a two-phase flow swirling method or a pressurized dissolution method.

An ozone water described in a sixth embodiment is the ozone water according to the first embodiment, in which the dissolution of the organic iron compound and the inorganic salt in the water with ozone-microbubbles generated is performed at an elapsed time of 20 minutes or longer after the redox potential of the water with ozone-microbubbles generated, which increases, reaches at least +600 mV.

An ozone water described in a seventh embodiment is the ozone water according to the first embodiment, in which when the ozone water filled in an airtight container under atmospheric pressure is stored under a temperature condition of 40° C., the half-life of ozone is 3 days or longer.

An ozone water described in an eighth embodiment is the ozone water according to the first embodiment, in which when the ozone water filled in an airtight container under atmospheric pressure is cryopreserved for 1 month or longer under a temperature condition of −20° C. and then naturally thawed at a normal temperature (25° C.), the water recovers the state of the ozone water before the cryopreservation.

An ozone water described in a ninth embodiment is the ozone water according to the first embodiment, which is not irritating to mammal skin, has no oral acute toxicity to mammals, and has a sterilizing effect and a deodorant effect.

A method for producing an ozone water of the present invention comprises, as described in a tenth embodiment, dissolving 0.1 µM to 1 mM of an organic iron compound and 1 to 300 mM of an inorganic salt in a water with ozone-microbubbles generated using an ozone gas at a concentration of 1 to 300 g/Nm³.

A method for producing an ozone water described in an eleventh embodiment is the method for producing an ozone water according to the tenth embodiment, in which the generation of ozone-microbubbles is achieved by using a microbubble generator that can generate microbubbles having a particle size of 5 to 50 µm.

A method for producing an ozone water described in a twelfth embodiment is the method for producing an ozone water according to the tenth embodiment, in which the dissolution of the organic iron compound and the inorganic salt in the water with ozone-microbubbles generated is performed at an elapsed time of 20 minutes or longer after the redox potential of the water with ozone-microbubbles generated, which increases, reaches at least +600 mV.

Effect of the Invention

According to the present invention, an ozone water having enhanced storage stability and a method for producing the ozone water can be provided.

MODE FOR CARRYING OUT THE INVENTION

An ozone water of the present invention is produced by dissolving 0.1 µM to 1 mM of an organic iron compound and 1 to 300 mM of an inorganic salt in a water with ozone-microbubbles generated using an ozone gas at a concentration of 1 to 300 g/Nm$^3$.

In the production of the ozone water of the present invention, at the beginning, a water with ozone-microbubbles generated is prepared. The generation of ozone-microbubbles in water may be achieved according to any technique known per se and may be performed using a microbubble generator that employs a two-phase flow swirling method or a pressurized dissolution method that can generate microbubbles having a particle size of 5 to 50 µm. In the case where a two-phase flow swirling method is employed, a vortex flow having a radius of 10 cm or less is forcibly caused using a rotator or the like, and a gas-liquid mixture containing ozone that is to be contained in microbubbles is struck against an obstacle, such as a wall surface, or against a fluid having a different relative velocity, whereby a gas body obtained in the vortex flow is dispersed under the process of distraction of the vortex. As a result, ozone-microbubbles desired can be generated. In addition, in the case where a pressurized dissolution method is employed, ozone that is to be contained in microbubbles is dissolved in water at a high pressure of 2 atm or more and then depressurizing to the atmospheric pressure. As a result, ozone-microbubbles can be generated from dissolved gas under supersaturated conditions. In this case, at the pressure reduction region, a large number of vortexes having a radius of 1 mm or less are generated utilizing the water flow and an obstacle, and a large number of gas-phase nuclei (bubble nuclei) are formed due to the oscillation of water molecules in the central region of the vortex flow. At the same time, following the supersaturated conditions, the gas body in water is diffused toward these bubble nuclei resulting in the growth of the bubble nuclei. As a result, ozone-microbubbles desired can be generated in a large amount. Incidentally, ozone-microbubbles generated by these methods are microbubbles having a particle size of 50 µm or less. The particle size has a peak at 10 to 15 µm as measured with a laser-light-blocking liquid particle counter (e.g., LiQuilaz-E20 manufactured by SPM Co., etc.), and the number of microbubbles in the peak region is 1000/mL or more (see JP-A-2000-51107, JP-A-2003-265938, etc., if necessary). The ozone gas used for generating ozone-microbubbles in water is a gas prepared at a concentration of 1 to 300 g/Nm$^3$ using, for example, a commercially available oxygen source ozone generator. When an ozone gas having a concentration of less than 1 g/Nm$^3$ is used, it is not possible to efficiently generate a large amount of ozone-microbubbles in water. On the other hand, it is difficult to prepare an ozone gas having a concentration exceeding 300 g/Nm$^3$. Incidentally, the ozone gas may contain oxygen, nitrogen, or the like in addition to ozone.

Next, prescribed amounts of an organic iron compound and an inorganic salt are dissolved in the water with ozone-microbubbles generated. Specific examples of the organic iron compound include water soluble compounds, such as iron ammonium citrate, iron fulvate, iron acetate, heme iron, iron dextran, diethylenetriaminepentaacetic acid iron sodium salt, diethylenetriaminepentaacetic acid iron ammonium salt, ethylenediaminetetraacetic acid iron sodium salt, ethylenediaminetetraacetic acid iron ammonium salt, iron triethylenetetramine, dicarboxymethylglutamic acid iron sodium salt, ferrous citrate, iron sodium citrate, iron oxalate, ferrous succinate, iron sodium succinate citrate, ferrous pyrophosphate, ferric pyrophosphate, iron lactate, ferrous gluconate, ferrous formate, ferric formate, potassium ferric ammonium oxalate, ferrous ascorbate, and sodium ferric edetate. The amount of the organic iron compound dissolved is 0.1 µM to 1 mM. When the amount dissolved is less than 0.1 µM, the effect of dissolving may not be sufficiently attained. Meanwhile, when the amount exceeds 1 mM, enhancement of the effect of dissolving may not be expected with increase only in the cost, and in addition, iron hydroxide and the like may be produced and precipitated. The amount of the organic iron compound dissolved is desirably 1 to 100 µM.

By dissolving an inorganic salt in the water with ozone-microbubbles generated, microbubbles can shrink and then stably exist as nanobubbles having a particle size of, for example, 10 to 500 nm. Specific examples of the inorganic salt include water soluble compounds, such as sodium chloride, potassium chloride, magnesium chloride, and magnesium sulfate. The amount of the inorganic salt dissolved is 1 to 300 mM. When the amount dissolved is less than 1 mM, the effect of dissolving may not be sufficiently attained. Meanwhile, when the amount exceeds 300 mM, enhancement of the effect of dissolving may not be expected with increase only in the cost. The amount of the inorganic salt dissolved is desirably 10 to 100 mM.

The dissolution of the prescribed amounts of the organic iron compound and the inorganic salt in the water with ozone-microbubbles generated is desirably performed at an elapsed time of 20 minutes or longer after the redox potential of the water, which increases from an initial value of +300 mV to 500 mV by ozone-microbubbles being continuously generated, reaches at least +600 mV or higher, in that storage stability of the ozone water can be effectively enhanced (the increase in the redox potential comes to plateau at approximately +1000 mV). Also, after the prescribed amounts of the organic iron compound and the inorganic salt are dissolved in the water with ozone-microbubbles generated, ozone is desirably continuously supplied in the form of microbubbles for at least 5 minutes, desirably at least 30 minutes, and more desirably at least 1 hour, in that storage stability of the ozone water can be effectively enhanced.

The order of the dissolutions of the prescribed amounts of the organic iron compound and the inorganic salt in the water with ozone-microbubbles generated is not particularly limited, and the compounds may be dissolved at once, or may be dissolved stepwise. The pH of the water with ozone-microbubbles generated in which the prescribed amounts of the organic iron compound and the inorganic salt have been dissolved is desirably 3 to 10, and more desirably 5 to 9. The reason is as follows. Both the cases of too-high acidity and too-high alkalinity make the microbubbles and nanobubbles unstable and cause such bubbles to disappear while generating hydroxide radicals. In addition, the hydroxide radicals generated degrade the organic iron compound, and therefore storage stability of the ozone water may not be enhanced. The adjustment of the pH may be appropriately achieved with hydrochloric acid or sodium hydroxide.

In the ozone water of the present invention, ozone exists stably in water at a concentration of, for example, 1 to 50 mg/L, and the half-life thereof is 3 days or longer, for example, when the water filled in an airtight container under atmospheric pressure is stored under a temperature condition of 40° C. In addition, as for the ozone water of the present invention, for example, when the water filled in an airtight container under atmospheric pressure is cryopreserved for 1 month or longer under a temperature condition of −20° C. and then naturally thawed at a normal temperature (25° C.), the water recovers the state of the ozone water before the cryopreservation. Although the mechanism how the organic iron compound contributes to the stability of ozone in water is not exactly clear, the present inventor supposes the mechanism as follows. Iron ions contained in the organic iron compound are brought into a peroxidation state by the oxidative effect of the ozone supplied into the water in the form of microbubbles. The iron ions are attracted and trapped by an electrostatic effect around bubbles in the course of shrinkage of the microbubbles or around nanobubbles generated by the shrinkage, and held as one of components constituting an ion shell for a bubble, thereby stabilizing nanobubbles. The ozone water of the present invention can be utilized for various applications that are known as applications of ozone water. For example, the ozone water of the present invention is not irritating to mammal skin, has no oral acute toxicity to mammals, and has a sterilizing effect, a deodorant effect, and the like.

EXAMPLES

Hereinunder, the present invention will be described in detail with reference to the examples. However, the present invention should not be construed as being limited to the following descriptions.

Example 1

Ozone-microbubbles were generated in distilled water using a commercially available microbubble generator that employs a two-phase flow swirling method (compact bubble generator manufactured by AQUAAIR Co., Ltd.) that can generate microbubbles mainly having a particle size of 5 to 50 µm. An ozone gas that was prepared at a concentration of about 30 g/Nm$^3$ using a commercially available oxygen source ozone generator was supplied at about 100 mL/min to the microbubble generator so as to give an ozone concentration in water of about 5 mg/L. The redox potential of the water was confirmed to continuously increase from the initial value of about +500 mV by ozone-microbubbles being continuously generated, and then, at an elapsed time of 30 minutes after the redox potential reached +600 mV, 10 µM of iron ammonium citrate as an organic iron compound and 50 mM of sodium chloride as an inorganic salt were dissolved, and the pH was adjusted to 8 with sodium hydroxide. After that, ozone-microbubbles were further continuously generated for 1 hour. The ozone concentration of the thus produced ozone water of the present invention was 5 mg/L as measured by the KI method. It took about 2 hours to produce 5 L of the ozone water of the present invention.

Example 2

Ozone-microbubbles were generated in distilled water using a commercially available microbubble generator that employs a pressurized dissolution method (A-02 manufactured by Shigenkaihatsukenkyujyo, Inc.) that can generate microbubbles mainly having a particle size of 5 to 50 µm. An ozone gas that was prepared at a concentration of about 20 g/Nm$^3$ using a commercially available oxygen source ozone generator was supplied at about 100 mL/min to the microbubble generator so as to give an ozone concentration in water of about 5 mg/L. The redox potential of the water was confirmed to continuously increase from the initial value of about +500 mV by ozone-microbubbles being continuously generated, and then, at an elapsed time of 20 minutes after the redox potential reached +600 mV, 10 µM of iron ammonium citrate as an organic iron compound and 50 mM of magnesium sulfate as an inorganic salt were dissolved, and the pH was adjusted to 8 with sodium hydroxide. After that, ozone-microbubbles were further continuously generated for 1 hour. The ozone concentration of the thus produced ozone water of the present invention was 4 mg/L as measured by the KI method. It took about 1 hour to produce 5 L of the ozone water of the present invention.

Example 3

An ozone water of the present invention was produced in the same manner as in Example 1, except that iron fulvate was dissolved in place of iron ammonium citrate.

Example 4

The half-life of ozone of the ozone water of the present invention produced in Example 1 was investigated in the case where the water filled in a PET bottle as an airtight container under atmospheric pressure was stored under a temperature condition of 40° C. As a result, the half-life measured was 3 days or longer (half or more of the ozone remained after an elapsed time of 3 days).

Example 5

The ozone water of the present invention produced in Example 1 filled in a PET bottle as an airtight container under atmospheric pressure was cryopreserved for 1 month or longer under a temperature condition of −20° C. and then naturally thawed at a normal temperature (25° C.). As a result, the water recovered the state of the ozone water before the cryopreservation (even if the water was cryopreserved for 1 month before being thawed, the ozone concentration was the same as that before the cryopreservation).

Example 6

The ozone water of the present invention produced in Example 1 was allowed to stand in a dark place under a room temperature condition for 1 week. After that, DMPO (5,5-dimethyl-1-pyrroline N-oxide) which is a spin-trapping agent was added and hydrochloric acid was further added to measure the electron spin resonance (ESR) spectrum under a strongly acidic condition of pH 2. As a result, the spectrum of DMPO-OH which is a spin adduct (a spectrum that shows generation of hydroxide radicals) could be observed.

Example 7

Using the ozone water of the present invention produced in Example 1 as a specimen, a primary skin irritation test was conducted using a rabbit conforming to the OECD Guidelines for the Testing of Chemicals 404. As a result, no irritation was observed.

Example 8

The ozone water of the present invention produced in Example 1 was orally administered to a rat at a dose of 20 mg/kg for 14 days. As a result, no acute toxicity was observed.

Example 9

The sterilizing effect of the ozone water of the present invention produced in Example 1 against a pathogenic bacterium, Salmonella enteritidis was investigated. As a result, an excellent sterilizing effect was observed.

Example 10

An appropriate amount of the ozone water of the present invention produced in Example 1 was sprayed on cutting chips of PET bottles (industrial waste) which have an abnormal odor in summer. As a result, an excellent deodorant effect was shown.

Example 11

An ozone water of the present invention was produced in the same manner as in Example 1, except that iron ammonium citrate and sodium chloride were dissolved at an elapsed time of 1 hour after the redox potential of the water reached +600 mV by ozone-microbubbles being continuously generated in distilled water. As a result, the half-life of ozone was prolonged as compared with the ozone water of the present invention produced in Example 1.

Comparative Example 1

An ozone water was produced in the same manner as in Example 1, except that ozone was supplied by bubbling with a common aeration tube. The ozone water was filled in a PET bottle as an airtight container under atmospheric pressure and stored under a temperature condition of 40° C. As a result, at an elapsed time of 1 day after the start of the test, the ozone concentration was almost zero.

Comparative Example 1

An ozone water was produced in the same manner as in Example 1, except that iron ammonium citrate was not dissolved. The ozone water was filled in a PET bottle as an airtight container under atmospheric pressure and stored under a temperature condition of 40° C. As a result, at an elapsed time of 3 hours after the start of the test, the ozone concentration was almost zero.

INDUSTRIAL APPLICABILITY

The present invention is industrially applicable in points of being capable of providing an ozone water having enhanced storage stability and a method for producing the ozone water.

The invention claimed is:

1. An ozone water, which is produced by dissolving 0.1 µM to 1 mM of an organic iron compound and 1 to 300 mM of an inorganic salt in a water with ozone-microbubbles generated using an ozone gas at a concentration of 1 to 300 g/Nm$^3$, wherein the organic iron compound is at least one selected from the group consisting of iron ammonium citrate, iron acetate, heme iron, iron dextran, diethylenetriaminepentaacetic acid iron sodium salt, diethylenetriaminepentaacetic acid iron ammonium salt, ethylenediaminetetraacetic acid iron sodium salt, ethylenediaminetetraacetic acid iron ammonium salt, iron triethylenetetramine, dicarboxymethylglutamic acid iron sodium salt, ferrous citrate, iron sodium citrate, iron oxalate, ferrous succinate, iron sodium succinate citrate, ferrous pyrophosphate, ferric pyrophosphate, iron lactate, ferrous gluconate, ferrous formate, ferric formate, potassium ferric ammonium oxalate, ferrous ascorbate, and sodium ferric edetate.

2. The ozone water according to claim 1, wherein the inorganic salt is at least one or more selected from the group consisting of sodium chloride, potassium chloride, magnesium chloride, and magnesium sulfate.

3. The ozone water according to claim 1, wherein the generation of ozone-microbubbles is achieved by using a microbubble generator that can generate microbubbles having a particle size of 5 to 50 µm.

4. The ozone water according to claim 3, wherein the microbubble generator is a microbubble generator that employs a two-phase flow swirling method or a pressurized dissolution method.

5. The ozone water according to claim 1, wherein the dissolution of the organic iron compound and the inorganic salt in the water with ozone-microbubbles generated is performed at an elapsed time of 20 minutes or longer after the redox potential of the water with ozone-microbubbles generated, which increases, reaches at least +600 mV.

6. The ozone water according to claim 1, wherein when the ozone water filled in an airtight container under atmospheric pressure is stored under a temperature condition of 40° C., the half-life of ozone is 3 days or longer.

7. The ozone water according to claim 1, wherein when the ozone water filled in an airtight container under atmospheric pressure is cryopreserved for 1 month or longer under a temperature condition of −20° C. and then naturally thawed at a temperature of 25° C., the ozone concentration of the ozone water is the same as that before the cryopreservation.

8. The ozone water according to claim 1, wherein the ozone water is not irritating to mammal skin, has no oral acute toxicity to mammals, and has a sterilizing effect and a deodorant effect.

* * * * *